(12) United States Patent
Gokaraju et al.

(10) Patent No.: US 11,986,506 B2
(45) Date of Patent: *May 21, 2024

(54) DIETARY SUPPLEMENTS FOR INHIBITING PDE5 AND INCREASING cGMP LEVELS

(71) Applicant: LAILA NUTRACEUTICALS, Vijayawada (IN)

(72) Inventors: Ganga Raju Gokaraju, Vijaywada (IN); Rama Raju Gokaraju, Vijayawada (IN); Trimurtulu Golakoti, Vijayawada (IN); Kiran Bhupathiraju, Vijayawada (IN); Venkata Kanaka Ranga Raju Gokaraju, Vijayawada (IN); Krishanu Sengupta, Vijayawada (IN); Venkata Krishna Raju Alluri, Vijayawada (IN)

(73) Assignee: LAILA NUTRACEUTICALS, Vijayawada (IN)

( * ) Notice: Subject to any disclaimer, the term of this patent is extended or adjusted under 35 U.S.C. 154(b) by 393 days.

This patent is subject to a terminal disclaimer.

(21) Appl. No.: 16/479,798

(22) PCT Filed: Jan. 19, 2018

(86) PCT No.: PCT/IN2018/050028
§ 371 (c)(1),
(2) Date: Jul. 22, 2019

(87) PCT Pub. No.: WO2018/134848
PCT Pub. Date: Jul. 26, 2018

(65) Prior Publication Data
US 2021/0338757 A1    Nov. 4, 2021

(30) Foreign Application Priority Data
Jan. 20, 2017 (IN) .............................. 201741002329

(51) Int. Cl.
*A61K 36/22* (2006.01)
*A23L 33/105* (2016.01)
*A61K 9/00* (2006.01)
*A61K 36/38* (2006.01)
*A61K 45/06* (2006.01)
*A61P 15/10* (2006.01)

(52) U.S. Cl.
CPC ............ *A61K 36/22* (2013.01); *A23L 33/105* (2016.08); *A61K 9/0095* (2013.01); *A61K 36/38* (2013.01); *A61K 45/06* (2013.01); *A61P 15/10* (2018.01); *A61K 2236/15* (2013.01); *A61K 2236/333* (2013.01); *A61K 2236/51* (2013.01); *A61K 2236/53* (2013.01)

(58) Field of Classification Search
None
See application file for complete search history.

(56) References Cited

U.S. PATENT DOCUMENTS

| | | | |
|---|---|---|---|
| 7,927,633 B2 * | 4/2011 | Swilling | A61K 36/8967 424/725 |
| 9,050,292 B2 | 6/2015 | Baron et al. | |
| 9,486,482 B2 | 11/2016 | Chaudhary et al. | |
| 2010/0247434 A1 | 9/2010 | Greenway et al. | |
| 2014/0128405 A1 | 5/2014 | Chervinsky | |
| 2015/0238552 A1 * | 8/2015 | Banerjee | A61K 36/185 424/756 |

FOREIGN PATENT DOCUMENTS

| | | | | |
|---|---|---|---|---|
| CN | 105380979 A | 3/2016 | | |
| IN | 201201376 I1 * | 12/2014 | | |
| WO | 1994028902 | 12/1994 | | |
| WO | WO-2009002298 A1 * | 12/2008 | ........... | A23L 1/2121 |

OTHER PUBLICATIONS

Deepak (Pharmacognosy Magazine (2012), vol. 8, No. 30, pp. 116-123).*
"POM Wonderful—POM Mango" product (https://www.youtube.com/watch?v=2C6XHAX5p9l&t=49s—2015).*

* cited by examiner

*Primary Examiner* — Susan Hoffman
(74) *Attorney, Agent, or Firm* — Kramer & Amado, P.C.

(57) ABSTRACT

The invention discloses synergistic compositions comprising extracts, fractions or pure compounds derived from at least two herbs selected from *Punica granatum, Mangifera indica* and *Garcinia mangostana* for inhibiting the expression/production/activity of Phosphodiesterase 5 (PDE5) enzyme or for increasing cGMP levels in a male subject. The invention further discloses a method of inhibiting the expression/production/activity of Phosphodiesterase 5 (PDE5) enzyme, increasing cGMP levels and sexual arousal, treating/alleviating various aspects of male sexual dysfunction or impotence such as erectile dysfunction, loss of libido, or orgasm/ejaculation disorders in a male subject by using a suitable dose of synergistic composition comprising extracts, fractions or pure compounds derived from at least two herbs selected from *Punica granatum, Mangifera indica* and *Garcinia mangostana*.

18 Claims, 3 Drawing Sheets

DIETARY SUPPLEMENTS FOR INHIBITING PDE5 AND INCREASING cGMP LEVELS

TECHNICAL FIELD OF THE INVENTION

The present invention relates to synergistic compositions comprising extracts, fractions or pure compounds derived from at least two herbs selected from *Punica granatum, Mangifera indica* and *Garcinia mangostana* for inhibiting the expression/production/activity of Phosphodiesterase 5 (PDE5) enzyme or for increasing cGMP levels, thereby useful in treating/alleviating various aspects of male sexual dysfunction or impotence such as erectile dysfunction, loss of libido, premature ejaculation, delayed or inhibited ejaculation and priapism or painful erections in a male subject. The present invention also relates to a synergistic composition useful for improving male sexual health and sexual functions and vitality. The invention further relates to a method of inhibiting the expression/production/activity of Phosphodiesterase 5 (PDE5) enzyme, increasing cGMP levels and sexual arousal, and thereby useful in treating/alleviating various aspects of male sexual dysfunction or impotence such as erectile dysfunction, loss of libido, or orgasm/ejaculation disorders in a male subject by using a suitable dose of synergistic composition comprising at least two ingredients selected from the extracts, fractions or pure compounds derived from the plants parts of *Punica granatum, Mangifera indica* and *Garcinia mangostana*.

BACKGROUND OF THE INVENTION

The role of selective PDE5 inhibitors in the treatment of erectile dysfunction has been well documented in the prior art. Although many synthetic drugs are available to treat Sexual dysfunction, their drawbacks include higher costs and serious adverse effects. This has prompted the researchers to focus on the development of effective natural treatments.

WO 1994028902 A1 discloses Pyrazolopyrimidinones for the treatment of impotence and one of them is sildenafil citrate, which is marketed as Viagra and is the popular oral treatment for erectile dysfunction. But it is contraindicated in patients on nitrates treatment.

U.S. Pat. No. 9,486,482B2 discloses an herbal composition comprising extracts of herbal ingredients of *Tribulus terrestris, Withania somnifera, Curculigo orchioides, Mucuna pruriens, Asparagus adscendens, Asteracantha longifolia, Asphaltum*, and optionally the extracts of *Piper longum* and *Anacyclus pyrethrum* for the treatment of disorders associated with Male Sexual Dysfunction.

CN105380979A discloses an herbal composition comprising dodder seed along with *Ganoderma* and epimedium herb for the treatment of erectile dysfunction. Patent application no. 1553/DEL/2014 discloses an herbal composition for the treatment of erectile dysfunction, which consists of Nux vomica and Damiana.

In addition, various devices such as vacuum devices, penile implants are available, but benefit only those patients whose function has been severely impaired. Bruising, skin breakdown, and penile pain may occur while using these devices.

Due to the limitations and adverse effects of existing treatments and limited availability of efficient and safer herbal treatments for treating different forms of sexual dysfunction, there is a need in the art to provide highly potent and safe alternative treatments comprising herbal extracts/fraction for the treatment of various aspects of male sexual dysfunction, especially for long term supplementation.

OBJECT OF THE INVENTION

The principal object of the present invention is to provide synergistic herbal compositions comprising at least two ingredients selected from the extracts, fractions or pure compounds derived from the plant parts of *Punica granatum, Mangifera indica* and *Garcinia mangostana* for inhibiting the expression/production/activity of Phosphodiesterase 5 (PDE5) enzyme or for increasing cGMP levels and sexual arousal, and hence useful in treating/alleviating various forms of male sexual dysfunction which include but not limited to erectile dysfunction, premature ejaculation, loss of libido, orgasm/ejaculation disorders, delayed or inhibited ejaculation and priapism or painful erections.

Yet another object of the present invention is to provide methods to treat/alleviate various forms of male sexual dysfunction which include but not limited to erectile dysfunction, loss of libido, premature ejaculation, delayed or inhibited ejaculation and priapism or painful erections, wherein the method comprises supplementing the male with an effective dose of a herbal synergistic composition comprising at least two ingredients selected from the extracts, fractions or pure compounds derived from the plant parts of *Punica granatum, Mangifera indica* and *Garcinia mangostana* that inhibits expression/production/activity of Phosphodiesterase 5 (PDE5) enzyme, increases cGMP levels or sexual arousal.

SUMMARY OF THE INVENTION

In line with the above objects, the present invention provides synergistic compositions comprising at least two ingredients selected from the extracts, fractions or pure compounds derived from the plants parts of *Punica granatum, Mangifera indica* and *Garcinia mangostana* for inhibiting the expression/production/activity of Phosphodiesterase 5 (PDE5) enzyme or for increasing cGMP levels and sexual arousal and thus useful for treating/alleviating various forms of male sexual dysfunction which include but not limited to erectile dysfunction, loss of libido, orgasm/ejaculation disorders, premature ejaculation, poor ejaculation, delayed or inhibited ejaculation and priapism or painful erections.

In another aspect, the present invention provides use of a synergistic composition comprising at least two ingredients selected from the extracts, fractions or pure compounds derived from the plant parts of *Punica granatum, Mangifera indica* and *Garcinia mangostana* for inhibiting the expression/production/activity of Phosphodiesterase 5 (PDE5) enzyme or for increasing cGMP levels and sexual arousal, thereby useful for treating/alleviating various forms of male sexual dysfunction which include but not limited to erectile dysfunction, loss of libido, orgasm/ejaculation disorders, premature ejaculation, poor ejaculation, delayed or inhibited ejaculation and priapism or painful erections, wherein, the compositions further contain optionally at least one component selected from the excipients, diluents, biological agent(s) and aphrodisiac agent(s).

In the other aspect, the invention provides a method of inhibiting the expression/production/activity of Phosphodiesterase 5 (PDE5) enzyme or increasing cGMP levels and sexual arousal thereby treating/alleviating various forms of male sexual dysfunction which include but not limited to erectile dysfunction, loss of libido or orgasm/ejaculation disorders, premature ejaculation, poor ejaculation, delayed or inhibited ejaculation and priapism or painful erections, in a male subject, wherein, the method comprises supplementing the subject with a suitable dose of a synergistic composition comprising at least two ingredients selected from the extracts, fractions or pure compounds derived from the plants parts of *Punica granatum, Mangifera indica* and *Garcinia mangostana*.

DESCRIPTION OF THE INVENTION

Male sexual arousal is a complex process involving brain, hormones, emotions, nerves, muscles and blood vessels. Hence, a problem associated with any of these can cause sexual dysfunction. Examples of male sexual dysfunction or impotence include erectile dysfunction, loss of libido, orgasm/ejaculation disorders, premature ejaculation, delayed ejaculation, poor ejaculation and priapism or painful erections. Erectile dysfunction is a common type of male sexual dysfunction characterized by the inability to develop or maintain an erection of the penis during the course of sexual activity. Male penis contains two symmetrical compartments or corpora; each one is called corpus cavernosum and changes in the blood flow in these compartments controls the erection of the penis. The corpora cavernosa consists of vascular sinusoids and these are surrounded by cavernous smooth muscle. A penile erection can be described as a hydraulic effect created by blood flow entering and being retained in these sponge like cavernous smooth muscle bodies within the penis.

At the time of sexual stimulation, Nitric Oxide (NO) is released in the cavernous smooth muscle and it activates Guanylate Cyclase (GC), which in turn catalyzes the conversion of GTP to cGMP. The cGMP activates certain intracellular Protein Kinases, which leads to cavernous smooth muscle relaxation, followed by blood flow into corpus cavernosum and ultimately erection of the penis. Phosphodiesterases (PDEs) are enzymes, which metabolize cGMP and inactivate them. Phosphodiesterase 5 (PDE5) is the predominant phosphodiesterase present in the corpus cavernosum, which is specific to the cGMP present in the cavernous smooth muscle. As the catalytic site of PDE5 activates degradation of cGMP, the inhibitors of PDE5 enzyme potentiate endogenous increases in cGMP in the cavernous smooth muscle, which in turn facilitates the erection of penis.

Based on this prior knowledge, the inventors of the current application randomly screened a large number of plant extracts for their efficacy in inhibiting Phosphodiesterase 5 (PDE5) enzyme using the PDE-Glo™ Phosphodiesterase assay. The extracts, fractions and pure compounds derived from the plant parts of *Punica granatum, Mangifera indica* and *Garcinia mangostana*, among other plant extracts showed potent inhibition of PDE5 activity as summarized in table 1 for selected extracts. The methanol extract obtained from *Punica granatum* fruit rind (LN16048), 80% methanol extract of *Garcinia mangostana* fruit rind (LI80013) and 50% ethanol extract of *Mangifera indica* bark (LN16053) for example exhibited potent inhibition of PDE5 enzyme with half inhibitory concentrations (IC50 values) of 0.212±0.0323 µg/mL, 0.107±0.027 µg/mL and 0.61±0.0219 µg/mL respectively. The ethanol extracts of *Acacia auriculiformis* leaf (LN16056) and *Myristica fragrans* seed (Nut) (LN16055), methanol extracts of *Chloroxylon swietenia* leaf (LI16600) and *Curcuma longa* root (LI01106) and 90% ethanol extract of *Cissus quadrangularis* stem (LI89033) also exhibited potent inhibition of PDE5 enzyme with half inhibitory concentrations (IC50 values) of 0.144±0.0708 µg/mL, 4.1 µg/mL, 4.8 µg/mL, 5.03±0.027 µg/mL and 4.38±0.42 µg/mL respectively and the results summarized in table 1.

Figure 1:
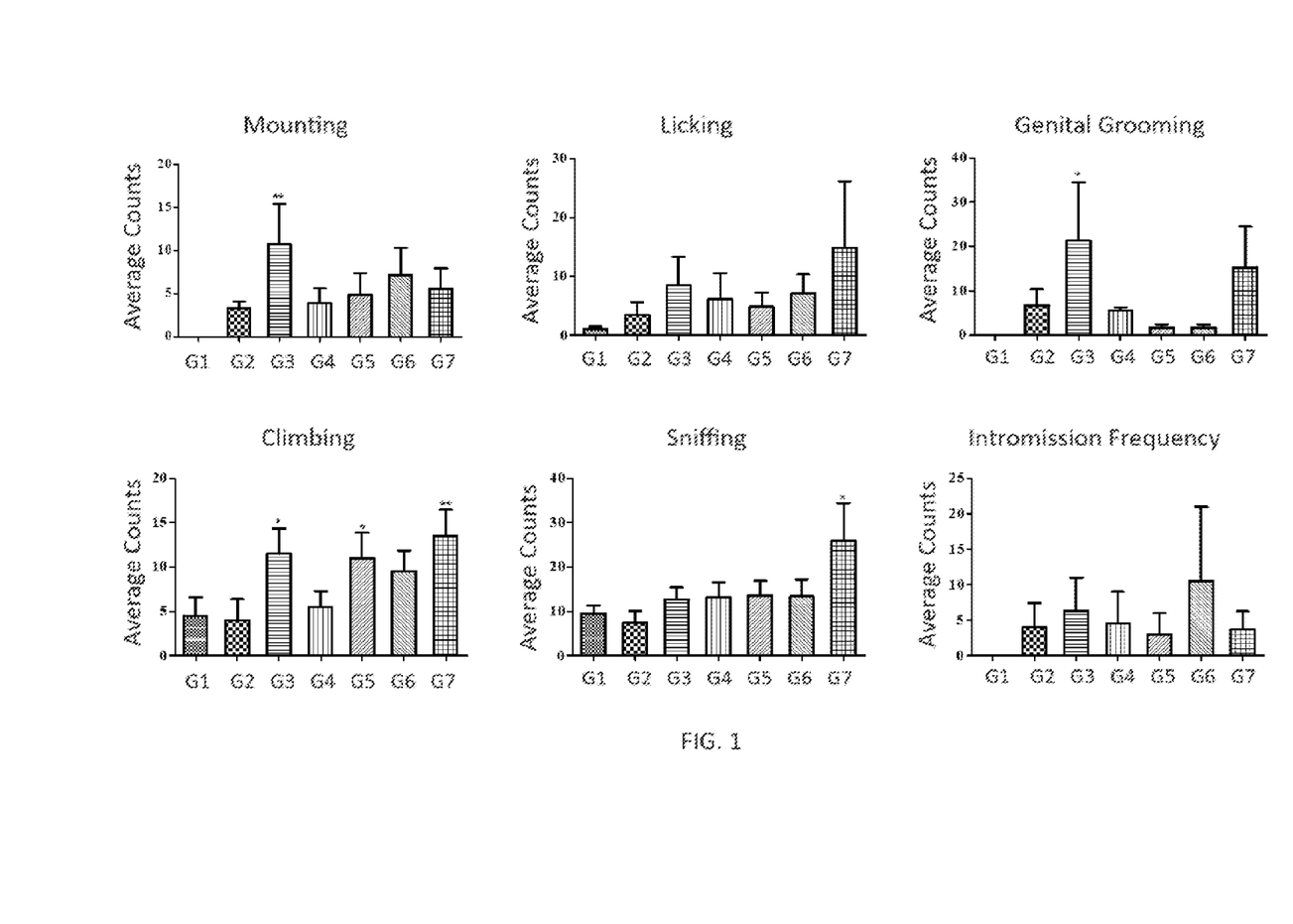
FIG. 1: Precopulatory and copulatory counts in the treatment groups supplemented with vehicle control (G1), LI80013 (250 mg/kg; G2), LN16048 (250 mg/kg; G3), LI16600 (G4), LN16053 (150 and 300 mg/kg; G5 & G6) and sildenafil citrate (10 mg/kg; G7). Data are expressed as mean±S.E.M of 6 rats per group. *$p<0.05$, **$p<0.01$ vs normal control (G1) by One-way ANOVA followed by Dunnett's Test.

The extracts of the current invention were then evaluated for their efficacy in vivo to stimulate sexual behavior in male rats. Briefly, healthy Sprague Dawley rats were acclimatized and randomized into various treatment groups (G1 to G6) as summarized in table 5. These animals were introduced to mating with female counterparts, which were previously treated with 100 µg/rat of estradiol benzoate and 1 mg/rat of progesterone at approximately 48 hours and 4 hours respectively prior to mating. The male rats were treated orally with one of vehicle (G1), extracts of *Garcinia mangostana* rind (LI80013, 250 mg/kg; G2), *Punica granatum* rind (LN16048, 250 mg/kg; G3), *Chloroxylon swietenia* (LI16600, 250 mg; G4), *Mangifera indica* (LN16053, 150 mg; G5) or *Mangifera indica* (LN16053, 300 mg/kg; G6) or sildenafil citrate (10 mg/kg; G7) at approximately 1 hr prior to introduction to mating and the male sexual behaviour was evaluated for a period of 30 minutes. The scored test parameters include frequency of licking, anogenital sniffing, climbing, genital grooming, mounting and intromission. The results are summarized in tables 6 and 7, and depicted in FIG. 1. The scores for precopulatory behavior such as licking, sniffing, genital grooming and climbing counts were significantly higher in animals of treatment groups supplemented with LN16048 and LN16053, when compared to the control group. Similarly, the copulatory behaviours such as mounting and intromission frequency were also increased in LN16048 and LN16053 supplemented groups, when compared to control group. The increase in mounting frequency and intromission frequency are considered the indices of both libido and potency. In mounting parameter, LN16048 showed statistical significance (p value <0.05), when compared to control group. The extracts LI80013 and LI16600 also exhibited improved scores of precopulatory and copulatory parameters.

Figure 2:
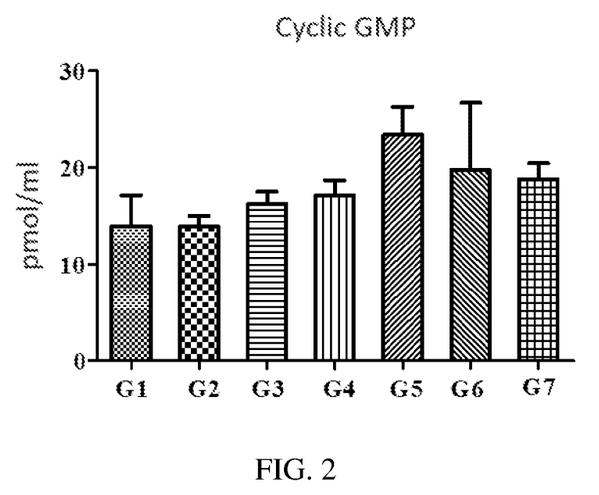
FIG. 2: Cyclic GMP levels (cGMP) in the plasma of treatment groups supplemented with vehicle control (G1), LI80013 (250 mg/kg; G2), LN16048 (250 mg/kg; G3), LI16600 (G4), LN16053 (150 and 300 mg/kg; G5 & G6) and sildenafil citrate (10 mg/kg; G7). Data are expressed as mean±S.E.M of 6 rats per group.

After 30 minutes of mating period, blood sample were collected from all animals, plasma separated and subjected to cyclic-GMP estimation using cyclic GMP ELISA Kit supplied by Cayman (Cat No 581022) as per the procedure provided by the manufacturer. The plasma cyclic GMP modulation data is summarized in Table 8 and depicted in FIG. 2. The plasma cyclic GMP levels were increased significantly in the treatment groups supplemented with LN16048, LI16600 and LN16053, when compared to the control group. The mean cyclic GMP levels were 13.85, 13.87, 16.21, 17.12, 23.38, 19.76 and 18.79 pmol/mL respectively in control group (G1), LI80013 (G2), LN16048 (G3), LI16600 (G4), LN16053 (150 mg; G5), LN16053 (300 mg; G6) and sildenafil citrate (G7) groups. Overall, the data revealed that LI80013, LN16048, LI16600 and LN16053 have the potential to increase the concentration of cGMP in systemic circulation and in turn can stimulate the sexual behavior in male rats.

The inventors then prepared several compositions containing at least two ingredients selected from the extracts, fraction or pure compounds derived from *Punica granatum*, *Mangifera indica*, *Garcinia mangostana*, and tested the compositions for their potential to inhibit PDE5 enzyme activity in comparison with their respective individual ingredients. It was found unexpectedly that the compositions of the present invention showed better inhibition of PDE5 activity compared to the individual ingredients suggesting synergistic action between their individual ingredients. For example, the composition-3 containing methanol extract of *Punica granatum* rind (LN16048) and 50% ethanol extract of *Mangifera indica* bark (LN16053) in 1:2 ratio showed 65.87% inhibition of PDE5 at 0.3 µg/ml, when compared to the inhibitions 46.36% and 40.45% exhibited by its corresponding individual extracts ingredients derived from *Punica granatum* rind (LN16048) and *Mangifera indica* bark (LN16053) respectively at the same concentration. Other compositions, Composition-1, Composition-2 and Composition-4 comprising these ingredients at ratios 2:1, 1:1 and 1:3 respectively have also shown synergistic efficacy in inhibiting the PDE5 enzyme as summarized in table 2.

It was also found surprisingly that compositions comprising other solvent extracts or fractions derived from other plant parts of *Punica granatum* and *Mangifera indica* also exhibited synergistic inhibition of PDE5. For example, the composition containing 70% ethanol extract of *Punica granatum* rind (LN18143) in combination with 80% ethanol extract of *Mangifera indica* leaf (LN18147) at different ratios showed more potent inhibition of PDE5 enzyme when compared to the efficacy shown by the corresponding individual extracts derived from *Punica granatum* rind and *Mangifera indica* leaf. The *Punica granatum* rind 70% ethanol extract (LN18143) and *Mangifera indica* leaf 80% ethanol extract (LN18147) at 2.5 µg/mL showed 30.73% and 30.76% inhibition of PDE5 respectively. The composition-7 containing these extracts at 1:1 ratio showed 71.81% inhibition at 5 µg/mL concentration, which is significantly better than the additive effect (30.73%+30.76%=61.49%) from these two ingredients, suggesting synergistic inhibition of PDE5 by *Punica granatum* rind 70% ethanol extract and *Mangifera indica* leaf 80% ethanol extract. These two ingredients also showed synergism when combined at ratios, 3:1, 2:1, 1:2 and 1:3 as shown by the superior PDE5 inhibitory effects exhibited by the compositions-5, 6, 8 and 9 respectively. Similarly, other compositions (Compositions-10 to 14) containing *Punica granatum* fruit rind 70% ethanol extract in combination with *Mangifera indica* bark 80% ethanol extract (LN18141) at different ratios also showed synergistic effect. The results for the foregoing studies are summarized in Table 3.

In addition, *Punica granatum* rind extract also exhibited synergism when combined with extracts derived from *Garcinia mangostana*. *Punica granatum* rind 70% ethanol extract and *Garcinia mangostana* rind 50% ethanol extract (LN18142) showed 34.94% and 25.25% inhibition of PDE5 respectively at 0.1 µg/mL. The composition-17 containing these extracts at 1:1 ratio showed significantly better efficacy with 77.46% inhibition of PDE5 at 0.2 µg/mL concentration, which is better than the additive effect (34.94%+25.25%=60.19%) from these two ingredients at 0.1 µg/mL concentration, suggesting synergistic effect between *Punica granatum* rind 70% ethanol extract and *Garcinia mangostana* 50% ethanol extract. These two ingredients also showed synergism when combined at other ratios, viz., 3:1, 2:1, 1:2 and 1:3 as shown by the improved PDE5 inhibitory effects exhibited by the compositions-15, 16, 18 and 19 respectively as summarized in Table 4.

Similarly, synergism was also observed between the extracts derived from *Garcinia mangostana* and *Mangifera indica*. For example, the compositions-20 and 24 containing *Mangifera indica* leaf 80% ethanol extract (LN18147) and *Garcinia mangostana* 50% ethanol extract (LN18142) in 3:1 and 1:3 ratio manifested PDE5 inhibitions of 84.27% and 81.19% respectively, which are over and above the additive effects 73.47% and 64.71% calculated from the inhibitions shown by individual ingredients corresponding to the above compositions as summarized in table 4.

Figure 3:
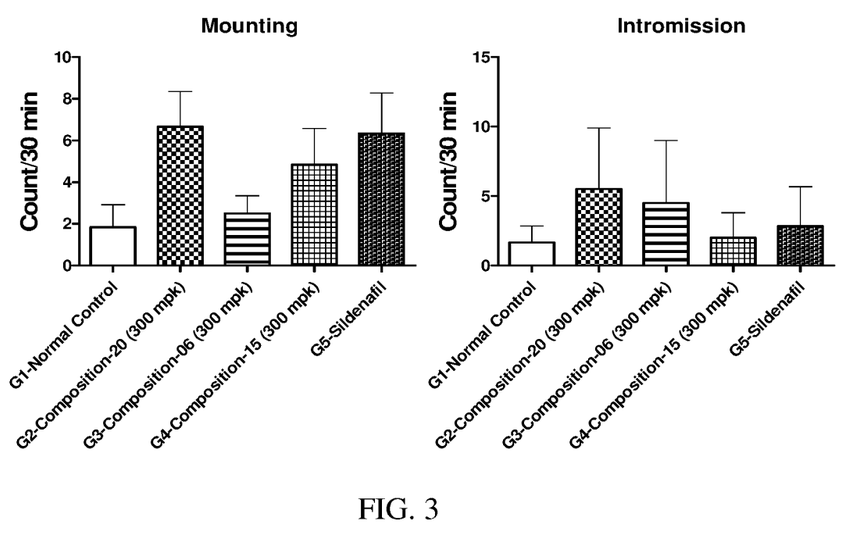
FIG. 3: Copulatory counts in the treatment groups supplemented with vehicle control (G1), composition-20 (300 mg/kg; G2), composition-6 (300 mg/kg; G3), composition-15 (300 mg/kg; G4), and sildenafil citrate (10 mg/kg; G5). Data are expressed as mean±S.E.M of 6 rats per group. *$p<0.05$, **$p<0.01$ vs normal control (G1) by One-way ANOVA followed by Dunnett's Test.

A few selected compositions (compositions-6, 15 and 20) of the current invention were then evaluated for their efficacy in vivo to stimulate sexual behavior in male rats using the experimental as disclosed above for the testing of individual ingredients. The experimental data indicated that the copulatory behaviours such as mounting and intromission frequency were increased in treatment groups supplemented with composition-6, composition-15 or composition-20, when compared to control group as summarized in FIG. 3.

Hence, the forgoing results demonstrate that extracts or fractions derived from *Punica granatum*, *Garcinia mangostana* and *Mangifera indica* and the compositions containing the same effectively inhibits the expression/production/activity of Phosphodiesterase 5 (PDE5) enzyme, increases cGMP levels and sexual arousal, and thus useful for treating various forms of male sexual dysfunction and impotence, which include but not limited to erectile dysfunction, loss of libido, orgasm/ejaculation disorders, premature ejaculation, poor ejaculation, delayed or inhibited ejaculation and priapism or painful erections.

Therefore in the important embodiment, the invention discloses synergistic compositions comprising at least two ingredients selected from the extracts, fractions and pure compounds derived from the plant parts of *Punica granatum*, *Garcinia mangostana*, and *Mangifera indica*, for inhibiting the expression/production/activity of Phosphodiesterase 5 (PDE5) enzyme, for increasing cGMP levels and sexual arousal, thereby useful in treating/alleviating various forms of male sexual dysfunction and impotence, which include but not limited to erectile dysfunction, loss of libido, orgasm/ejaculation disorders, premature ejaculation, poor ejaculation, delayed or inhibited ejaculation and priapism or painful erections.

In another exemplary embodiment the invention discloses the synergistic compositions comprising at least two ingredients selected from the extracts, fractions and pure compounds derived from the plant parts of *Punica granatum*, *Garcinia mangostana*, and *Mangifera indica*, wherein the synergistic compositions contain optionally at least one additional component selected from the group consisting of biologically active natural ingredients selected from other PDE5 inhibitor(s), known aphrodisiac agent(s), biological agent(s); pharmaceutically acceptable active ingredients, vitamins, minerals; pharmaceutically or nutraceutically or dietically acceptable, excipients, carriers or diluents.

In other exemplary embodiment, the invention discloses the synergistic compositions comprising at least two ingredients selected from the extracts, fractions and pure compounds derived from the plant parts of *Punica granatum, Garcinia mangostana*, and *Mangifera indica*, wherein, the compositions further contained optionally at least one other PDE5 inhibitor(s) selected from the extracts and fractions derived from *Acacia auriculiformis, Cissus quadrangularis, Curcuma longa, Chloroxylon swietenia* or *Myristica fragrans*.

In another exemplary embodiment, the invention discloses the synergistic compositions comprising at least two ingredients selected from the extracts, fractions and pure compounds derived from the plant parts of *Punica granatum, Garcinia mangostana*, and *Mangifera indica*, wherein, the compositions further contained optionally at least one additional ingredient selected from pharmaceputically or dietetically acceptable excipients, carriers and diluents, which include but not limited glucose, fructose, sucrose, maltose, yellow dextrin, white dextrin, aerosil, microcrystalline cellulose, neusilin, calcium stearate, magnesium stearate, sorbitol, stevioside, corn syrup, lactose, citric acid, tartaric acid, malic acid, succinic acid, lactic acid, L-ascorbic acid, dl-alpha-tocopherol, glycerin, propylene glycol, glycerin fatty ester, poly glycerin fatty ester, sucrose fatty ester, sorbitan fatty ester, propylene glycol fatty ester, *Acacia*, carrageenan, casein, gelatin, pectin, agar, vitamin B group, nicotinamide, calcium pantothenate, amino acids, proteins, calcium salts, pigments, flavors, preservatives, distilled water, saline, aqueous glucose solution, alcohol, propylene glycol and polyethylene glycol, various animal and vegetable oils, white soft paraffin, paraffin, flavorants, colourants and wax.

In another embodiment, the invention discloses the synergistic compositions comprising at least two ingredients selected from the extracts, fractions and pure compounds derived from the plant parts of *Punica granatum, Garcinia mangostana*, and *Mangifera indica*, wherein, the weight of *Punica granatum* derived component varies in the range of 10%-90% in the composition, the weight of *Mangifera indica* derived component varies in the range of 90%-10% and the weight of *Garcinia mangostana* derived component varies in the range of 90%-10%.

In another embodiment, the invention discloses the synergistic compositions comprising at least two ingredients selected from the extracts, fractions and pure compounds derived from the plant parts of *Punica granatum, Garcinia mangostana*, and *Mangifera indica*, wherein, the *Punica granatum* derived extract or fraction contains punicalagins in the range of 1 to 20% by HPLC method of analysis and/or total polyphenols in the range of 5 to 50% by UV method of analysis, the *Mangifera indica* derived extract or fraction contains 1 to 30% mangiferin and the *Garcinia mangostana* derived extract or fraction contains 1 to 30% α and γ mangostins.

In another embodiment, the invention provides synergistic compositions comprising at least two extracts, fractions or pure compounds derived from the herbs selected from *Punica granatum, Mangifera indica* and *Garcinia mangostana* for inhibiting the expression/production/activity of Phosphodiesterase 5 (PDE5) enzyme or for increasing cGMP levels and sexual arousal, thereby useful in treating/alleviating various forms of male sexual dysfunction and impotence, which include but not limited to erectile dysfunction, loss of libido, orgasm/ejaculation disorders, premature ejaculation, poor ejaculation, delayed or inhibited ejaculation and priapism or painful erections, wherein solvents used for preparing the extracts and fractions can be selected from but not limited to C1-C5 alcohols, like ethanol, methanol, n-propanol, isopropyl alcohol; ketones like acetone, methylisobutyl ketone, chlorinated solvents like methylene dichloride and chloroform, water and mixtures thereof; C1-C7 hydrocarbons such as hexane; esters like ethyl acetate and the like and mixtures thereof.

In another embodiment, the invention provides synergistic compositions comprising at least two extracts, fractions or pure compounds derived from the herbs selected from *Punica granatum, Mangifera indica* and *Garcinia mangostana* for inhibiting the expression/production/activity of Phosphodiesterase 5 (PDE5) enzyme or for increasing cGMP levels and sexual arousal, thereby useful in treating/alleviating various forms of male sexual dysfunction and impotence, which include but not limited to erectile dysfunction, loss of libido, orgasm/ejaculation disorders, premature ejaculation, poor ejaculation, delayed or inhibited ejaculation and priapism or painful erections, wherein, the plant parts used for preparing the extracts can be selected from leaves, stems, tender stems, tender twigs, aerial parts, whole fruit, fruit rind, seed, flower heads, root, bark, hardwood or whole plant or mixtures thereof.

In another embodiment the present invention provides synergistic compositions comprising at least two extracts, fractions or pure compounds derived from the herbs selected from *Punica granatum, Mangifera indica* and *Garcinia mangostana* for inhibiting the expression/production/activity of Phosphodiesterase 5 (PDE5) enzyme or for increasing cGMP levels, where in the extracts or fractions are standardized to at least one phytochemical reference marker compound or biological active marker in the extract or fraction.

In another embodiment, the extracts, fractions or composition(s) of the present invention may be formulated into a dosage form selected from dry powder form, liquid form, beverage, food product, dietary supplement or any suitable form such as tablet, a capsule or a soft chewable tablet or gummy bar.

In another embodiment of the invention, the extracts or fractions or composition(s) as disclosed above can be formulated into nutritional/dietary supplements that can be contemplated/made into the dosage form of healthy foods, or food for specified health uses such as solid food like chocolate or nutritional bars, semisolid food like cream or jam, or gel and also beverage and the like, such as refreshing beverage, lactic acid bacteria beverage, drop, candy, chewing gum, gummy candy, yoghurt, ice cream, pudding, soft adzuki bean jelly, jelly, cookie, tea, soft drink, juice, milk, coffee, cereal, snack bar and the like.

In yet another embodiment, the present invention provides a method of inhibiting the expression/production/activity of Phosphodiesterase 5 (PDE5) enzyme, increasing cGMP levels and sexual arousal, and to treat/alleviate at least one condition related to male sexual dysfunction and impotence, wherein the conditions related to male sexual dysfunction and impotence are selected from erectile dysfunction, loss of libido, premature ejaculation, delayed or inhibited ejaculation and priapism or painful erections, wherein the method comprises treating the subject with a suitable dose of a synergistic composition comprising at least two components selected from the extract(s), fraction(s), active compound(s) and phytochemicals or mixtures thereof derived from the plant parts of *Punica granatum*, *Mangifera indica* and *Garcinia mangostana* and optionally containing at least one additional component selected from the group consisting of biologically active natural ingredients selected from other PDE5 inhibitor(s), known aphrodisiac agent(s), biological agent(s); pharmaceutically acceptable active ingredients, vitamins, minerals; pharmaceutically or nutraceutic ally or dietically acceptable, excipients, carriers or diluents.

In another embodiment the extracts or fractions or composition(s) of the present invention can be delivered in the form of controlled release tablets, using controlled release polymer-based coatings by the techniques including nanotechnology, microencapsulation, colloidal carrier systems and other drug delivery systems for obtaining the desired therapeutic benefit.

Those of ordinary skilled in the art will appreciate that changes could be made to the embodiments described above without departing from the broad inventive concept thereof. It is understood, therefore, that this invention is not limited to the particular embodiments or examples disclosed herein, but is intended to cover modifications within the objectives and scope of the present invention as defined in the specification. The presented examples illustrate the invention, but they should not be considered to limit the scope of the invention in any way.

Example 1

Preparation of methanol (LN16048) and aqueous alcohol (60% methanol; LN16047) extracts of *Punica granatum* dried fruit rind: Dried *Punica granatum* fruit rind (100 g) was pulverized and the powder was extracted with methanol (400 mL) at 80° C. temperatures for 2 h. The extract was filtered and the spent raw material was re-extracted twice with methanol (2×300 mL) under similar extraction conditions. The combined extract was fine filtered and concentrated under vacuum to obtain a residue of methanol extract (LN16048; 25.6 g, Punicalagins 12%). The aqueous methanol extract (LN16047; 31.4 g) was obtained by adopting similar procedure using 60% methanol as extraction solvent.

Example-2

Preparation of 70% ethanol (LN18143) extract, ethanol extract (LN17135) and water extract of *Punica granatum* dried fruit rind: *Punica granatum* dried fruit rind (0.1 Kg) was pulverized into a coarse powder and extracted with 70% ethanol (700 mL) for 1 hour at ambient temperature. The extract was separated by filtration and the spent raw material was extracted twice using 500 mL of 70% ethanol for each extraction. All the extracts were combined and the combined 70% ethanol extract was fine filtered. The clear extract was evaporated at 40° C. under vacuum on rotary evaporator to obtain thick concentrate (~50 ml), which was subjected to freeze drying for 24 hours to get *Punica granatum* fruit rind 70% ethanol extract (LN18143) as a brown colour powder (35.0 g). The ethanol extract (LN17135; 17.5 g) and water extract (LN18140; 39.0 g) were obtained using the similar procedure as above using ethanol and water as extraction solvents respectively.

Example 3

Preparation of *Punica granatum* rind juice water extract from fresh raw material and its purified fractions: A fresh sample of 250 g of fresh *Punica granatum* peel was pulverized along with 500 mL of water and the pulpy syrup was filtered through filter cloth. The process was repeated two more times with the spent material using 300 mL water each time. The filtrates were combined and fine filtered through a nylon cloth, followed by filtration on super cell to get 1.2 L of juice extract. This extract was concentrated under vacuum on Rota vapor to obtain *Punica granatum* fresh rind juice extract (50 g) containing 9% Punicalagins & 4% Pro anthocyanidins).

Example 4

Preparation of different solvent extracts of *Mangifera indica* bark and leaf: The dried raw material of *Mangifera indica* bark (100 g) was pulverized and the powder was extracted with 50% ethanol (700 mL) using continuous percolation process at ambient temperature for 1.5 h in a soxhlet apparatus. The extract was removed from Soxhlet and the spent raw material was re-extracted twice with 50% ethanol (2×500 mL) under similar conditions. The extracts were combined, fine filtered and the filtrate was concentrated on a rotary evaporator under vacuum at ambient temperature. The concentrate was finally subjected to freeze-drying to obtain 50% ethanol extract of *Mangifera indica* bark (LN16053; 17.3 g). The water extract (LN16052; 9.9 g); ethanol extract (LN16054; 9.55 g, Mangiferin 18%) and 80% ethanol extract (LN 18141; 11.8 g) were prepared by similar extraction procedure using water, ethanol and 80% ethanol respectively as extraction solvents. *Mangifera indica* leaf 80% ethanol extract (LN18147; 15.9 g), water extract (LN18138; 11.8 g) and ethanol extract (LN18139; 7.50 g) were also prepared by using the aforementioned procedure with 80% ethanol, water and ethanol respectively as extraction solvents.

Example 5

*Garcinia mangostana* rind raw material was pulverized and extracted with 5 volumes (weight/volume with respect to raw material) of 80% MeOH an extractor using a continuous percolation process for 16-20 hrs. The extract was filtered through a nylon cloth and the filtrate was concentrated under vacuum to >50% total solids. This thick paste extract was washed twice with 2 volumes of water and the residue was dried under vacuum at 60-65° C. for 8-12 h to obtain *Garcinia mangostana* 80% methanol extract (L180013) as a powder residue with yield corresponds to an herb to product (HPR) ratio around 10:1.

Example 6

Preparation of *Garcinia mangostana* fruit rind 50% ethanol, ethanol and water extracts: Dried plant material was pulverized into coarse powder and extracted with 50% ethanol (700 mL) for 1 hour at ambient temperature. The extract was separated by filtration and the spent raw material was extracted twice using 500 mL of 50% ethanol per extraction. All the extracts were combined, the combined 50% ethanol extract was fine filtered, and the clear solution was evaporated at 40° C. under vacuum. The thick solution (~50 ml) so obtained was subjected to Freeze drying to yield *Garcinia mangostana* fruit rind 50% ethanol extract (LN18142) as a light brown colour residue (15.0 g). The ethanol extract (LN18144; 15.0 g) and water extract (LN18146; 7.5 g) were prepared by similar extraction procedure using ethanol and water respectively as extraction solvents.

Example 7

Preparation of *Cissus quadrangularis* 90% ethanol extract (L189033): The dried plant material of *Cissus quadrangularis* stem parts (1 kg) was pulverized to a coarse powder and extracted with 90% EtOH (5 L) at reflux condition for 1.5 Hrs. The extract filtered through a filter cloth and the residue was subjected to re-extraction process three more times using 90% EtOH under similar extraction conditions using 5 L of solvent each time. The extracts were combined, fine filtered through a nylon cloth and concentrated under vacuum on a rotary evaporator to obtain a thick paste containing 46-50% total solids (TS). The thick paste was subjected to vacuum drying at 50-55° C. for 8-10 h to give *Cissus quadrangularis* 90% ethanol extract (L189033) as a thick paste (75.8 g).

Example 8

Preparation of methanol extracts of *Curcuma longa* root (LIO1106) and *Chloroxylon swietenia* leaf (L116600): The root raw material of *Curcuma longa* (1 kg) were pulverized and the powder was extracted with methanol (5 L) at reflux temperature for 2 h in a round bottomed flask. The extract was filtered and the spent raw material was re-extracted twice with methanol (2×4 L) under similar conditions. The combined extract was fine filtered and concentrated under vacuum to obtain a thick paste having 70-75% TS. The paste was dried in a vacuum oven at 50-55° C. under vacuum to obtain a residue (98.0 g; LIO1106). The methanol extract of *Chloroxylon swietenia* leaf (L116600) was prepared using similar extraction procedure to obtain 118 g extract from 1 kg of *Chloroxylon swietenia* leaf raw material.

Example 10

Preparation of ethanol extracts of *Myristica fragrans* seed (LN16055) and *Acacia auriculiformis* aria parts (LN16056): *Myristica fragrans* seed (Nut) raw material (100 g) was pulverized and the powder was extracted with ethanol (500 mL) using continuous percolation process at ambient temperature for 1.5 h in a soxhlet apparatus. The extract was removed from Soxhlet and the spent raw material was re-extracted twice with ethanol (2×400 mL) under similar conditions. The extracts were combined, fine filtered and the filtrate was concentrated on a rotary evaporator under vacuum at ambient temperature to obtain ethanol extract of *Myristica fragrans* seed (LN16055; 13 g). The ethanol extract of *Acacia auriculiformis* ariel parts (LN16056) was prepared using similar extraction procedure to obtain 10.5 g extract from 100 g of *Acacia auriculiformis* aria parts raw material.

Example 11

Preparation of compositions containing at least two herbs selected from *Punica granatum, Mangifera indica* and *Garcinia mangostana.*

Composition-1: The Composition-1 was prepared by combining *Punica granatum* fruit rind methanol extract (LN16048) and *Mangifera indica* bark 50% ethanol extract (LN16053) in the ratio of 2:1.

Composition-2: The composition-2 was prepared by combining *Punica granatum* fruit rind methanol extract (LN16048) and *Mangifera indica* bark 50% ethanol extract (LN16053) in the ratio of 1:1.

Composition-3: The composition-3 was prepared by combining *Punica granatum* fruit rind methanol extract (LN16048) and *Mangifera indica* bark 50% ethanol extract (LN16053) in the ratio of 1:2.

Composition-4: The composition-4 was prepared by combining *Punica granatum* fruit rind methanol extract (LN16048) and *Mangifera indica* bark 50% ethanol extract (LN16053) in the ration of 1:3.

Composition-5: The composition-5 was prepared by combining *Punica granatum* fruit rind 70% ethanol extract (LN18143) and *Mangifera indica* leaf 80% ethanol extract (LN18147) in 3:1 ratio.

Composition-6: The composition-6 was prepared by combining *Punica granatum* fruit rind 70% ethanol extract (LN18143) and *Mangifera indica* leaf 80% ethanol extract (LN18147) in 2:1 ratio.

Composition-7: The composition-7 was prepared by combining *Punica granatum* fruit rind 70% ethanol extract (LN18143) and *Mangifera indica* leaf 80% ethanol extract (LN18147) in 1:1 ratio.

Composition-8: The composition-8 was prepared by combining *Punica granatum* fruit rind 70% ethanol extract (LN18143) and *Mangifera indica* leaf 80% ethanol extract (LN18147) in 1:2 ratio.

Composition-9: The composition-9 was prepared by combining *Punica granatum* fruit rind 70% ethanol extract (LN18143) and *Mangifera indica* leaf 80% ethanol extract (LN18147) in 1:3 ratio.

Composition-10: The composition-10 was prepared by combining *Mangifera indica* bark 80% ethanol extract in (LN18141) and *Punica granatum* fruit rind 70% ethanol extract (LN18143) in 3:1 ratio.

Composition-11:—The composition-11 was prepared by combining *Mangifera indica* bark 80% ethanol extract in (LN18141) and *Punica granatum* fruit rind 70% ethanol extract (LN18143) in 2:1 ratio.

Composition-12:—The composition-12 was prepared by combining *Mangifera indica* bark 80% ethanol extract in (LN18141) and *Punica granatum* fruit rind 70% ethanol extract (LN18143) 1:1 ratio.

Composition-13:—The composition-13 was prepared by combining *Mangifera indica* bark 80% ethanol extract in (LN18141) and *Punica granatum* fruit rind 70% ethanol extract (LN18143) 1:2 ratio.

Composition-14:—The composition-14 was prepared by combining *Mangifera indica* bark 80% ethanol extract in (LN18141) and *Punica granatum* fruit rind 70% ethanol extract (LN18143) 1:3 ratio.

Composition-15:—The composition-15 was prepared by combining *Punica granatum* fruit rind 70% ethanol extract (LN18143) and *Garcinia mangostana* fruit rind 50% ethanol extract (LN18142) in 3:1 ratio.

Composition-16:—The composition-16 was prepared by combining *Punica granatum* fruit rind 70% ethanol extract (LN18143) and *Garcinia mangostana* fruit rind 50% ethanol extract (LN18142) in 2:1 ratio.

Composition-17:—The composition-17 was prepared by combining *Punica granatum* fruit rind 70% ethanol extract (LN18143) and *Garcinia mangostana* fruit rind 50% ethanol extract in (LN18142) 1:1 ratio.

Composition-18:—The composition-18 was prepared by combining *Punica granatum* fruit rind 70% ethanol extract (LN18143) and *Garcinia mangostana* fruit rind 50% ethanol extract in (LN18142) 1:2 ratio.

Composition-19:—The composition-19 was prepared by combining *Punica granatum* fruit rind 70% ethanol extract (LN18143) and *Garcinia mangostana* fruit rind 50% ethanol extract in (LN18142) 1:3 ratio.

Composition-20:—The composition-21 was prepared by combining *Mangifera indica* leaf 80% ethanol extract (LN18147) and *Garcinia mangostana* fruit rind 50% ethanol extract (LN18142) in 3:1 ratio.

Composition-21:—The composition-21 was prepared by combining *Mangifera indica* leaf 80% ethanol extract (LN18147) and *Garcinia mangostana* fruit rind 50% ethanol extract (LN18142) in 2:1 ratio.

Composition-22:—The composition-22 was prepared by combining *Mangifera indica* leaf 80% ethanol extract (LN18147) and *Garcinia mangostana* fruit rind 50% ethanol extract in (LN18142) 1:1 ratio.

Composition-23:—The composition-23 was prepared by combining *Mangifera indica* leaf 80% ethanol extract (LN18147) and *Garcinia mangostana* fruit rind 50% ethanol extract in (LN18142) 1:2 ratio.

Composition-24:—The composition-24 was prepared by combining *Mangifera indica* leaf 80% ethanol extract (LN18147) and *Garcinia mangostana* fruit rind 50% ethanol extract in (LN18142) 1:3 ratio.

Composition-25:—The composition-25 was prepared by combining *Punica granatum* fruit rind water extract (LN18140) and *Mangifera indica* bark 80% ethanol extract in (LN18141) 1:1 ratio.

Composition-26:—The composition-26 was prepared by combining *Punica granatum* fruit rind 70% ethanol extract (LN18143) and *Mangifera indica* bark water extract (LN16052) in 2:1 ratio.

Example 12

Evaluation of Phosphodiesterase 5A (PDE5) inhibition efficacy of the extracts of *Punica granatum* peel (LN16048), *Garcinia mangostana* rind (L180013), *Acacia auriculiformis* aerial parts (LN16056), *Cissus quadrangularis* stem (L189033), *Curcuma longa* root (L101106), *Chloroxylon swietenia* leaf (L116600), *Myristica fragrans* seed(Nut) (LN16055), *Mangifera indica* bark (LN16053) and the compositions-1 to 26:

Biochemical evaluation of phosphodiesterase 5A (PDE5A) inhibition activities of the test samples (individual ingredients disclosed above and their compositions) were performed using PDE-Glo™ Phosphodiesterase assay kit (Promega Corporation, Madison, WI, USA) according to the manufacturer's protocol. Briefly, the PDE-Glo™ Phosphodiesterase assay was initiated in a reaction mixture containing different concentrations of the test samples, 5 nM PDE5A enzyme (Enzo life sciences, Farmingdale, NY, USA) and 10 μM cGMP substrate. Sildenafil citrate (Axxora, San Dieago, CA, USA) was reacted at various concentrations (5 to 20 nM) in place of the test samples, and considered as the positive control. The reaction mixture was incubated for 60 minutes at room temperature. The PDE reaction was terminated by adding PDE-Glo™ termination buffer (2.5 μL) containing IBMX (3-isobutyl-1-methylxanthine). Thereafter, PDE-Glo™ detection solution (2.5 μL) and Kinase-Glo® reagent (10 μL) were added to the reaction mixtures in sequence and incubated further for 5 min in dark. Finally, the complete reaction mixtures were transferred to a 384-well white plate (Sigma, St. Louis, MO, USA) and luminescence was measured in a microplate luminometer (Perkin Elmer, Waltham, MA, USA). The emitted light intensity (relative luminescence unit or RLU) was proportional to PDE activity in the reaction. Percentage inhibition of PDE5A activity of the test sample was calculated using following formula:

% inhibition in PDE5A activity in test sample=[RLU in (E+S)−RLU in test sample]/RLU in (E+S)× 100.

E and S stand for Enzyme and Substrate, respectively. The percentage inhibitions of PDE5 activity shown by different test compounds and their composition are summarized in tables 1 to 4.

TABLE 1

| PDE5 inhibitory Efficacy of test compounds | | |
| --- | --- | --- |
| Test Sample details | Sample ID | Inhibition of PDE5 Activity, IC50, (Mean ± SD) |
| *Garcinia mangostana* 80% methanol extract | LI80013 | 0.107 ± 0.027 μg/mL |
| *Punica granatum* methanol extracts | LN16048 | 0.212 ± 0.0323 μg/mL |
| *Mangifera indica* hydroalcohol ethanol extract | LN16053 | 0.61 ± 0.0219 μg/mL |
| *Cissus quadrangularis* methanol extract | LI89033 | 4.38 ± 0.42 μg/mL |
| *Curcuma longa* ethanol extract | LI01106 | 5.03 ± 0.27 μg/mL |
| *Acacia auriculiformis* ariel parts | LN16056 | 0.144 ± 0.0708 μg/mL |
| *Chloroxylon swietenia* leaf methanol extract | LI16600 | 4.8 μg/mL |
| *Myristica fragrans* seed(Nut) ethanol extract | LN16055 | 4.1 μg/mL |

TABLE 2

| Synergistic inhibition of PDE5 by inventive composition | | |
| --- | --- | --- |
| Sample ID | Treatment Conc. (ng/ml) | % Inhibition of PDE5 Enzyme activity |
| LN16048 | 33 | 0.70 |
|  | 100 | 33.38 |
|  | 300 | 46.36 |
| LN16053 | 33 | 8.55 |
|  | 100 | 21.76 |
|  | 300 | 40.45 |
| Composition-1 | 300 | 53.45 |
| Composition-2 | 300 | 64.30 |
| Composition-3 | 33 | 10.22 |
|  | 100 | 42.87 |
|  | 300 | 65.87 |
| Composition-4 | 33 | 30.70 |
|  | 100 | 49.63 |
|  | 300 | 61.45 |

TABLE-3

| Composition # | dose (µg/ml) | LN18143 µg/ml | % Inhibition | LN18147 µg/ml | % Inhibition | Ratio | % Inhibition of PDE5 Enzyme activity Additive (Calculated) | Observed |
|---|---|---|---|---|---|---|---|---|
| Composition-5 | 5 | 3.75 | 46.10 | 1.25 | 15.38 | 3:1 | 61.48 | 73.64 |
| Composition-6 | 5 | 3.33 | 40.94 | 1.67 | 20.55 | 2:1 | 61.49 | 71.11 |
| Composition-7 | 5 | 2.5 | 30.73 | 2.5 | 30.76 | 1:1 | 61.49 | 71.81 |
| Composition-8 | 5 | 1.67 | 20.53 | 3.33 | 40.98 | 1:2 | 61.51 | 66.62 |
| Composition-9 | 5 | 1.25 | 15.37 | 3.75 | 46.15 | 1:3 | 61.52 | 75.09 |
| | | LN18141 | | LN18143 | | | | |
| Composition-10 | 1 | 0.75 | 15.85 | 0.25 | 12.77 | 3:1 | 28.62 | 43.99 |
| Composition-11 | 1 | 0.67 | 14.16 | 0.33 | 16.86 | 2:1 | 31.02 | 61.42 |
| Composition-12 | 1 | 0.5 | 10.57 | 0.5 | 25.55 | 1:1 | 36.12 | 55.21 |
| Composition-13 | 1 | 0.33 | 6.98 | 0.67 | 34.24 | 1:2 | 41.22 | 52.51 |
| Composition-14 | 1 | 0.25 | 5.28 | 0.75 | 38.32 | 1:3 | 43.6 | 53.01 |

TABLE-4

| Composition # | dose (µg/ml) | LN18143 µg/ml | % Inhibition | LN18142 µg/ml | % Inhibition | Ratio | % Inhibition of PDE5 Enzyme activity Additive (Calculated) | Observed |
|---|---|---|---|---|---|---|---|---|
| Composition-15 | 0.2 | 0.15 | 52.42 | 0.05 | 12.62 | 3:1 | 65.04 | 84.03 |
| Composition-16 | 0.2 | 0.13 | 45.43 | 0.07 | 17.67 | 2:1 | 63.1 | 80.07 |
| Composition-17 | 0.2 | 0.1 | 34.94 | 0.1 | 25.25 | 1:1 | 60.19 | 77.46 |
| Composition-18 | 0.2 | 0.07 | 24.46 | 0.13 | 32.82 | 1:2 | 57.28 | 87.05 |
| Composition-19 | 0.2 | 0.05 | 17.47 | 0.15 | 37.87 | 1:3 | 55.34 | 72.4 |
| | | LN18147 | | LN18142 | | | | |
| Composition-20 | 5 | 3.75 | 58.39 | 1.25 | 15.08 | 3:1 | 73.47 | 84.27 |
| Composition-24 | 5 | 1.25 | 19.46 | 3.75 | 45.25 | 1:3 | 64.71 | 81.19 |
| | | LN18140 | | LN18141 | | | | |
| Composition-25 | 1 | 0.5 | 4.98 | 0.5 | 4.77 | 1:1 | 9.75 | 12.26 |
| | | LN18143 | | LN16052 | | | | |
| Composition-26 | 1 | 0.67 | 41.45 | 0.33 | 9.43 | 2:1 | 50.88 | 68.36 |
| | 5 | 3.33 | 56.53 | 1.67 | 19.19 | 2:1 | 75.72 | 84.2 |

Example 13

Evaluation of efficacy of the extracts of *Punica granatum* rind (LN16048), *Garcinia mangostana* rind (L180013), *Chloroxylon swietenia* leaf (L116600) and *Mangifera indica* bark (LN16053) in stimulating sexual behavior and increasing cGMP levels in male rats: Sprague Dawley rats were acclimatized for 3 days and 42 healthy male rats were selected and randomized into various treatment groups as shown in the following table.

TABLE 5

Study design

| Group | Treatment details | Dose | N | Treatment duration (day) |
|---|---|---|---|---|
| G1 | Control | Vehicle | 6 | 1 |
| G2 | LI80013 | 250 | 6 | 1 |
| G3 | LI16048 | 250 | 6 | 1 |
| G4 | LI16600 | 250 | 6 | 1 |
| G5 | LN16053 | 150 | 6 | 1 |
| G6 | LN16053 | 300 | 6 | 1 |
| G7 | Sildenafil citrate | 10 | 6 | 1 |

Separately, a set of 42 healthy female rats were selected and each of them were treated with single dose of 100 µg of estradiol benzoate and 1 mg of progesterone at approximately 48 hours and 4 hours respectively prior to introduction to mating. The extracts were suspended in 0.5% sodium CMC solution and the male rats were treated orally with one of vehicle, L180013 (250 mg/kg), LN16048 (250 mg/kg), L116600 (250 mg/kg), LN16053 (150 and 300 mg/kg) or sildenafil citrate (10 mg/kg) at approximately 1 hr prior to introduction to mating.

One hour after test substance administration, each male rat was allowed to mate with a female rat in *oestrus* phase. Male sexual behaviour was measured for a period of 30 minutes with the aid of video recording. The scored test parameters include frequency of licking, anogenital sniffing, climbing, genital grooming, mounting, intromission and the results are summarized in tables 6 and 7, and depicted in FIG. 1. The results indicate that LN16048, L180013, L116600 and LN16053 at 150 and 300 mpk(mg/kg) improved the desire for sex in male animals as shown by the increase in counts of licking, sniffing, genital grooming, climbing, mounting and intromission frequency.

After 30 minutes of mating period, blood sample was collected from each animal, plasma separated and the cyclic-GMP content was estimated using cyclic GMP ELISA Kit supplied by Cayman (Cat No 581022) as per the procedure provided by the manufacturer. The plasma cyclic GMP modulation data was summarized in Table 8 and FIG. 2. Overall, the data revealed that LN16048 at a dose of 250 mg/kg and LN16053 at doses of 150 or 300 mg/kg body weight exhibited potential for stimulating sexual behavior in male rats through enhancing cGMP levels.

TABLE 6

Summary of mean pre-copulatory behavioral count

| Groups | Licking count Mean ± SE | Sniffing count Mean ± SE | Genital grooming count Mean ± SE | Climbing count Mean ± SE |
|---|---|---|---|---|
| G1-Normal Control | 1.08 ± 0.40 | 9.58 ± 1.85 | 0.00 ± 0.00 | 4.50 ± 2.13 |
| G2-LI80013 (250 mpk) | 3.50 ± 2.13 | 7.50 ± 2.59 | 6.67 ± 3.69 | 4.00 ± 2.38 |
| G3- LN16048 (250 mpk) | 8.50 ± 4.83 | 12.67 ± 2.70 | 21.33 ± 13.11* | 11.50 ± 2.87* |
| G4- LI16600 (250 mpk) | 6.17 ± 4.39 | 13.17 ± 3.44 | 5.50 ± 0.85 | 5.50 ± 1.77 |
| G5- LN16053 (150 mpk) | 4.83 ± 2.52 | 13.67 ± 3.23 | 1.67 ± 0.76 | 11.00 ± 2.85* |
| G6- LN16053 (300 mpk) | 7.17 ± 3.15 | 13.33 ± 3.89 | 1.67 ± 0.76 | 9.50 ± 2.38 |
| G7-Sildenafil citrate (10 mpk) | 14.83 ± 11.32 | 25.83 ± 8.55* | 15.33 ± 9.20 | 13.50 ± 2.96** |

Data are expressed as mean ± S.E.M of six rats per group. *p < 0.05, **p < 0.01 vs normal control (G1) by One-way ANOVA followed by Dunnett's Test.

TABLE 7

Summary of copulatory behavioral counts

| Groups | Mounting count Mean ± SE | Intromission frequency Mean ± SE |
|---|---|---|
| G1-Normal Control | 0.00 ± 0.00 | 0.00 ± 0.00 |
| G2-LI80013 (250 mpk) | 3.33 ± 0.71 | 4.00 ± 3.44 |
| G3- LN16048 (250 mpk) | 10.67 ± 4.77** | 6.33 ± 4.63 |
| G4- LI16600 (250 mpk) | 3.83 ± 1.76 | 4.50 ± 4.50 |
| G5- LN16053 (150 mpk) | 4.83 ± 2.52 | 3.00 ± 3.00 |
| G6- LN16053 (300 mpk) | 7.17 ± 3.15 | 10.50 ± 10.50 |
| G7-Sildenafil citrate (10 mpk) | 5.50 ± 2.43 | 3.67 ± 2.55 |

Data are expressed as mean ± S.E.M of six rats per group. **p < 0.01 vs normal control (G1) by One-way ANOVA followed by Dunnett's Test.

TABLE 8

Summary of cyclic GMP levels

| Groups | Cyclic GMP levels |
|---|---|
| G1-Normal Control | 13.85 ± 3.31 |
| G2-LI80013 (250 mpk) | 13.87 ± 1.14 |
| G3- LN16048 (250 mpk) | 16.21 ± 1.30 |
| G4- LI16600 (250 mpk) | 17.12 ± 1.55 |
| G5- LN16053 (150 mpk) | 23.38 ± 2.92 |
| G6- LN16053 (300 mpk) | 19.76 ± 6.98 |
| G7-Sildenafil citrate (10 mpk) | 18.79 ± 1.65 |

Example 14

Evaluation of efficacy of the compositions-6, 15 and 20 containing the extracts of *Punica granatum* rind (LN18143), *Garcinia mangostana* rind (L180013) and/or *Mangifera indica* leaf (LN18143) in stimulating sexual behavior: The copulatory behaviour in male rats was evaluated using the similar experimental procedure as described in Example 13. The data for the copulatory parameters, viz mounting and intromission obtained for the compositions-6, 15 and 20 is summarized in FIG. 3. The compositions showed significantly increased the mounting and/or intromission frequency suggesting their potential use for erectile dysfunction.

We claim:

1. An herbal composition, comprising at least two extracts selected from the group consisting of an extract of a fruit rind of *Punica granatum*, a bark or leaf extract of *Mangifera indica*, and an extract of a fruit rind of *Garcinia mangostana*;

wherein the herbal composition comprises:
 a mixture of the extract of the fruit rind of *Punica granatum* and the bark or leaf extract of *Mangifera indica* in a ratio ranging from 3:1 to 1:3;
 a mixture of the extract of the fruit rind of *Punica granatum* and the extract of the fruit rind of *Garcinia mangostana* in a ratio ranging from 3:1 to 1:3;
 a mixture of the bark or leaf extract of *Mangifera indica* and the extract of the fruit rind of *Garcinia mangostana* in a ratio ranging from 3:1 to 1:3; or
 a combination thereof;
 wherein each of the at least two extracts is an alcoholic or hydroalcoholic extract.

2. The herbal composition of claim 1, wherein the herbal composition is present in an amount effective for at least one of:
 inhibiting the expression or activity of Phosphodiesterase 5 (PDE5) enzyme,
 increasing cGMP levels,
 increasing sexual arousal, and
 treating one or more conditions related to male sexual dysfunction and impotence.

3. The herbal composition of claim 2, wherein the herbal composition is present in an amount effective for treating one or more conditions related to male sexual dysfunction, the conditions related to male sexual dysfunction being selected from the group consisting of erectile dysfunction, loss of libido, premature ejaculation, delayed or inhibited ejaculation, priapism or painful erections, impotence, and a combination thereof.

4. The herbal composition of claim 1, wherein the composition further contains at least one component selected from the group consisting of a PDE5 inhibitor, an aphrodisiac agent; a biological agent; a pharmaceutically acceptable active ingredient; a vitamin; a mineral; and a pharmaceutically acceptable excipient, carrier or diluent.

5. The herbal composition of claim 4, wherein the PDE5 inhibitor is selected from the group consisting of extracts of *Acacia auriculiformis, Cissus quadrangularis, Curcuma longa, Chloroxylon swietenia, Myristica fragrans*, and mixtures thereof.

6. The herbal composition of claim 4, wherein the excipient, carrier or diluent is selected from the group consisting of glucose, fructose, sucrose, maltose, yellow dextrin, white dextrin, fumed silica, microcrystalline cellulose, calcium stearate, magnesium stearate, sorbitol, stevioside, corn syrup, lactose, citric acid, tartaric acid, malic acid, succinic acid, lactic acid, L-ascorbic acid, dl-alpha-tocopherol, glycerin, propylene glycol, glycerin fatty ester, poly glycerin fatty ester, sucrose fatty ester, sorbitan fatty ester, propylene glycol fatty ester, *acacia*, carrageenan, casein, gelatin, pectin, agar, vitamin B group, nicotinamide, calcium pantothenate, amino acids, proteins, calcium salts, pigments, flavors, preservatives, distilled water, saline, aqueous glucose solution, alcohol, propylene glycol and polyethylene glycol, various animal and vegetable oils, white soft paraffin, paraffin, flavorants, colourants, wax, and mixtures thereof.

7. The herbal composition of claim 1, wherein each of the at least two extracts is obtained by extraction with a solvent selected from the group consisting of ethanol, methanol, n-propanol, isopropyl alcohol, and mixtures thereof.

8. The herbal composition of claim 1, wherein the herbal composition meets at least one of the following conditions:
the extract of the fruit rind of *Punica granatum* contains from 1% to 20% punicalagins;
the extract of the fruit rind of *Punica granatum* contains from 5% to 50% total polyphenols;
the bark or leaf extract of *Mangifera indica* contains from 1% to 30% mangiferin; and
the extract of the fruit rind of *Garcinia mangostana* contains from 1 to 30% α and γ mangostins.

9. The herbal composition of claim 8, wherein the extract of the fruit rind of *Punica granatum* contains from 1% to 20% punicalagins and from 5% to 50% total polyphenols.

10. The herbal composition of claim 8, wherein the bark or leaf extract of *Mangifera indica* contains from 1% to 30% mangiferin.

11. The herbal composition of claim 8, wherein the extract of the fruit rind of *Garcinia mangostana* contains from 1 to 30% α and γmangostins.

12. A method of inhibiting the expression or activity of a phosphodiesterase 5 (PDE5) enzyme or increasing cGMP levels in a subject in need thereof, comprising administering an effective amount of the herbal composition of claim 1 to the subject.

13. A method of treating a subject suffering from a condition related to male sexual dysfunction, comprising administering an effective amount of the herbal composition of claim 1 to the subject;
the condition related to male sexual dysfunction being selected from the group consisting of erectile dysfunction, loss of libido, premature ejaculation, delayed or inhibited ejaculation, priapism or painful erections, impotence, and a combination thereof.

14. A dosage form comprising the herbal composition of claim 1, wherein the dosage form is selected from the group consisting of a dry powder, a liquid, a beverage, a food product, a dietary supplement, a tablet, a soft chewable tablet, and a capsule.

15. The dosage form of claim 14, wherein the dosage form is a food product selected from the group consisting of chocolate or nutritional bars, semisolid foods, creams, jams or jellies, gels, beverages, a candy, a chewing gum, a gummy candy, yoghurt, ice cream, pudding, soft adzuki bean jelly, cookies, cereal, and a snack bar.

16. The dosage form of claim 14, wherein the dosage form is a beverage selected from the group consisting of a lactic acid bacteria beverage, a tea, a soft drink, a juice, milk, and coffee.

17. An herbal composition, comprising at least two of:
a fruit rind extract of *Punica granatum* containing from 1% to 20% punicalagins, from 5% to 50% total polyphenols, or a mixture thereof;
a bark or leaf extract of *Mangifera indica* containing from 1% to 30% mangiferin; and
a fruit rind extract of *Garcinia mangostana* containing from 1 to 30% α and γ mangostins;
wherein the herbal composition comprises:
a mixture of the fruit rind extract of *Punica granatum* and the bark or leaf extract of *Mangifera indica* in a ratio ranging from 3:1 to 1:3;
a mixture of the fruit rind extract of *Punica granatum* and the fruit extract of *Garcinia mangostana* in a ratio ranging from 3:1 to 1:3;
a mixture of the bark or leaf extract of *Mangifera indica* and the fruit rind extract of *Garcinia mangostana* in a ratio ranging from 3:1 to 1:3; or
a combination thereof.

18. The herbal composition of claim 1, wherein each of the at least two extracts is obtained by extraction with a hydroalcoholic solvent comprising water and an alcohol selected from the group consisting of ethanol, methanol, n-propanol, isopropyl alcohol, and mixtures thereof.

* * * * *